United States Patent [19]

Arisawa et al.

[11] Patent Number: 5,891,694
[45] Date of Patent: *Apr. 6, 1999

[54] METHOD FOR RECOVERING NUCLEIC ACID AND DEVICE FOR THE SAME PURPOSE

[75] Inventors: Junji Arisawa; Kazuyuki Kimura, both of Hokkaido; Masakatsu Sano, Kanagawa; Nobuo Katsuura, Kanagawa; Osamu Igarashi, Kanagawa; Atsushi Nakayama, Kanagawa, all of Japan

[73] Assignee: Nikko Kogyo Kabushiki Kaisha, Kanagawa, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 580,966

[22] Filed: Dec. 29, 1995

[30] Foreign Application Priority Data

May 19, 1995 [JP] Japan .................................. 7-121242
Sep. 11, 1995 [JP] Japan .................................. 7-233121

[51] Int. Cl.$^6$ ........................... C12N 13/00; C07H 21/02; C07H 21/04
[52] U.S. Cl. ..................... 435/173.7; 435/173.1; 435/173.6; 435/785.2; 435/91.1; 536/23.1; 536/23.7
[58] Field of Search ........................... 536/25.4, 27, 23.1, 536/23.7; 435/291, 173.6, 172.3, 173.1, 287, 289, 285.2, 91.1; 525/256, 260, 285; 204/182.3, 299, 301, 182.8, 180.1, 182.6, 288, 289

[56] References Cited

U.S. PATENT DOCUMENTS

| | | | |
|---|---|---|---|
| 5,098,843 | 3/1992 | Calvin | 435/287 |
| 5,384,022 | 1/1995 | Rajasekaran | 204/299 R |
| 5,415,758 | 5/1995 | Comeau | 204/299 |
| 5,427,664 | 6/1995 | Stoev et al. | 204/182.3 |
| 5,440,025 | 8/1995 | Marx et al. | 536/25.4 |
| 5,510,195 | 4/1996 | Sano et al. | 428/613 |

FOREIGN PATENT DOCUMENTS

| | | | |
|---|---|---|---|
| 7-68268 | 3/1995 | Japan | C02F 1/48 |
| 7-322899 | 12/1995 | Japan | C12Q 1/68 |

*Primary Examiner*—Marian C. Knode
*Assistant Examiner*—Datquan Lee
*Attorney, Agent, or Firm*—Fish & Richardson, P.C.

[57] ABSTRACT

This invention provides a method for recovering nucleic acids and a device for the same purpose, which method and device are capable of continuously recovering nucleic acids by enabling the recovery of nucleic acids in one simple operation. This nucleic acid recovering device comprises: a container to which a solution containing micro-organisms is supplied; electrodes which are made of a hollow fiber membrane coated with a conductive metal and which send electricity to the solution; a pulse oscillator which sends pulse waves to the electrodes; and a micropump which draws up the solution within the hollow fiber membrane coated with metal.

10 Claims, 8 Drawing Sheets

METHOD FOR RECOVERING NUCLEIC ACID AND DEVICE FOR THE SAME PURPOSE

BACKGROUND OF THE INVENTION

1. Field of the Invention

This invention relates to a method for recovering nucleic acids from a solution containing micro-organisms and to a device for the same purpose.

2. Description of the Prior Art

Due to the development of the technology of gene recombination in the medical industry, biological formulations are being manufactured by gene recombination. For example, many protein liquid factors, such as human insulin, interferon which is becoming widely used for the medical treatment of hepatitis, or interleukin which is regarded as a carcinostatic, are being used as medicines to remedy previously incurable disease. These protein factors are manufactured by incorporating a human gene into a fungus such as calibacillus, having the fungus produce the protein factors, and then either by incorporating a separate gene which ejects the object constituents out of the fungus or by dissolving the fungus with another enzyme to recover the object constituents.

However, since the above method requires several operational steps, a problem exists in that protein cannot be recovered continuously.

Accordingly, the official gazette of the Japanese Patent Laid-Open (Kokai) Publication No. HEI 7-68268 provides a protein recovering method and device thereof which enable the recovery of protein and various hormones in one continuous operation, and which also enable the continuous recovery of protein and various hormones. This official gazette also discloses a sterilization method and a device thereof which are capable of obtaining a desirable sterilizing performance achieved through the introduction of electricity for a short period of time, as well as a removal method and a device thereof capable of removing fungi after sterilization.

These days, due to rapid development of gene engineering, it has become a daily affair to remove objective genes and protein from recombined bacteria. In order to take out genes and protein, a method of dissolving fungi with enzymes or physically breaking fungi by using ultrasonic waves, etc. is used.

However, whilst the conventional method described in the above official gazette can achieve the sterilization and the efficient recovery of protein and various hormones from a solution containing micro-organisms, recovery of nucleic acids is not considered at all.

When objective protein and genes are taken out of bacteria by dissolving fungi with enzymes or by physically breaking fungi with ultrasonic waves, it is necessary to cease the culturing of bacteria at once, thereby resulting in the problem that protein and genes cannot be taken out efficiently.

SUMMARY OF THE INVENTION

This invention aims to solve the above-mentioned conventional problems. An objective of the invention is to provide a nucleic acid recovering method and device capable of continuously recovering nucleic acids by enabling the recovery of nucleic acids in one simple operation.

The nucleic acid recovering method of the invention is characterized by the technique of sending an electric current through a solution containing micro-organisms and then recovering nucleic acids from the solution. As the method involves the sending of electricity, direct current, alternating current, pulse waves, impulse waves, etc. can be used. It is preferable, however, to send electricity using pulse waves and direct current. Impulse waves herein used means pulse waves which are differentiated.

The nucleic acid recovering method of the invention provides a method for sending electricity through a solution containing micro-organisms and then recovering nucleic acids and protein from the solution.

In order to realize this invention, the nucleic acid recovering device of the invention is characterized in that it comprises: a container in which a solution containing micro-organisms is held; electrodes which send electricity to the solution; an energizing device for providing electricity to the electrodes; and a means of isolating the nucleic acids.

Moreover, the nucleic acid recovering device of the invention is characterized in that it comprises: a container in which a solution containing micro-organisms is held; electrodes which send an electricity to the solution; an energizing device for providing electricity to the electrodes; and a means of isolating nucleic acids and protein from the solution.

The energizing device may generate pulse waves or direct current. It is possible to compose the electrodes from a hollow fiber membrane coated with a conductive metal. It is also possible to chemically bond the conductive metal to the hollow fiber membrane.

Through ardent study of the nucleic acid recovering method, the inventors of this invention discovered that it is possible to continuously recover nucleic acids from a solution containing micro-organisms by sending electricity through the solution. Namely, when micro-organisms are energized, cell membranes of the micro-organisms partially suffer a dielectric breakdown and intercellular protoplasm flows out. Since the intercellular protoplasm contains nucleic acids, it is possible to recover such nucleic acids, which are the object to be recovered, through the recovery of the intercellular protoplasm. Energizing herein used includes sending electricity via direct current, alternating current, pulse waves, or impulse waves.

Specifically, as a result of examinations, the inventors of the invention reached the conclusion that nucleic acids can be efficiently recovered by sending electricity via pulse waves or direct current.

Moreover, the recovering method of this invention is capable of recovering both nucleic acids and protein.

This method can be performed by using the nucleic acid recovering device which comprises, for example: a container in which a solution containing micro-organisms is held; electrodes which send electricity to the solution; an energizing device for providing electricity to the electrodes; and a means for isolating nucleic acids. This nucleic acid recovering device can comprise an energizing device which generates pulse waves or direct current. Moreover, the nucleic acid recovering device can comprise electrodes consisting of a hollow fiber membrane coated with a conductive metal.

As examples of a method for coating the hollow fiber membrane with a conductive metal, there are conventionally known methods such as plating, evaporation and sputtering. Particularly, as previously proposed by the applicant of this invention (in the Japanese Patent Application No. HEI 3-59357), it is desirable to adopt a method of chemically bonding the conductive metal to the hollow fiber membrane.

The reason is that if the above method is used, the hollow fiber membrane will be coated with a large amount of the conductive metal and will become superior in electrical conductivity and, as a result, good sterilizing performance can be obtained. The type of metal to be used in this invention is not specifically limited as long as it is conductive. It is preferable, however, to use a disinfectant metal such as silver.

In order to chemically bond the conductive metal to the hollow fiber membrane, a method of etching the hollow fiber membrane and treating it with a metallic salt solution can be used. This allows the conductive metal to be chemically bonded to a porous resin which forms a hollow fiber membrane, which then allows the formation of a metal layer having strong bond strength. This makes it possible to coat the porous resin with a sufficient amount of the metal.

When the resin is etched in a high concentration solution, functional groups, such as carbon radicals, carboxyl groups (—COOH), carbonyl groups (—C=O), hydroxyl groups (—OH), sulfone groups (—$SO_3H$) and nitrile groups (—CN), which are capable of being chemically bonded to metal, are produced on the resin side. Functional groups are produced because of the dehydrogenation, oxidation, cleavage, hydrolysis, etc. of the resin. Such functional groups are bonded to metallic atoms or ions (M), whereby, for example, —CM, —COOM, —COM, —OM, —$SO_3M$, and —CMN are formed, and the metal is chemically bonded to the resin.

A description will now be given of the mechanism in which polypropylene is etched in a high concentration solution of chromic acid and sulfuric acid. As represented by the following reaction formula (1), oxygen in a nascent state is produced in the above mixed solution.

[Chemical Formula (1)]

$$2CrO_3 + H_2O \rightarrow H_2Cr_2O_7 \quad H_2Cr_2O_7 + 3H_2SO_4 \rightarrow Cr_2(SO_4)_3 + 4H_2O + O_2 + (O)$$

(O): oxygen in a nascent state

As represented by the following reaction formula (2), the oxygen in the nascent state oxidizes the tertiary carbon of polypropylene and turns it into hydroxyl groups. The hydroxyl groups form ionic bonding with ammonium ions ($NH_4^+$) in ammonia water. When they react with metallic atoms or ions, metal (M) is substituted by the ammonium ions, and is coordinated to or electrically bonded to oxygen atoms. Chemical bonding of —COM is thus produced, with the result that the metal is chemically bonded to the resin.

[Chemical Formula (2)]

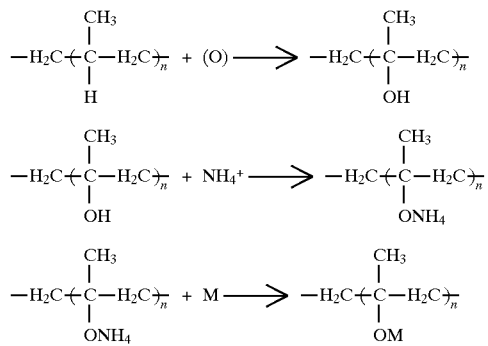

M: metal
(O): oxygen in a nascent state

When etching conditions become more severe, for example, when the concentration of chromic acid and sulfuric acid, or the reaction temperature increases, polypropylene cleaves, producing carboxyl groups, as represented by the following reaction formula (3). In this case also, in the same mechanism as with formula (2), metallic atoms or ions are coordinated to or are electrically bonded to the carboxyl groups. Because of the production of —COOM, the metal is chemically bonded to the resin. Chemical bonding between the metal and resin is thus produced in the boundary between the metallic layer and the resin. Owing to such chemical bonding, the resin is reliably coated with the metal, and the bond strength of the metallic layer is increased much more than that which is achieved by the conventional art.

[Chemical Formula 3]

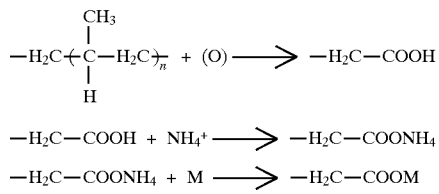

M: metal
(O): oxygen in a nascent state

An etching treatment liquid is preferably a liquid which can form functional groups capable of chemically bonding the metal to the resin, and includes a high concentration solution of chromic acid and sulfuric acid; a high concentration solution of sulfuric acid and nitric acid; a high concentration strong base, such as sodium hydroxide or potassium hydroxide; a high concentration solution of ammonium hydrogen fluoride and nitric acid, etc. The etching treatment liquid with a high concentration is desirable because it forms the functional groups on the resin. More specifically, the etching treatment liquid includes a mixed solution of 20–50% chromic acid and 10–40% sulfuric acid; 10–40% strong alkali; a mixed solution of 10–30% sulfuric acid and 10–30% nitric acid; and a mixed solution of 10–40% ammonium hydrogen fluoride and 40–70% nitric acid.

It is desirable for the resin to have a reaction zone capable of forming functional groups which can be chemically bonded to metal in the etching treatment liquid. More specifically, especially desirable are polypropylene possessing tertiary carbon; ABS possessing an unsaturated bond; polysulfone and polyethersulfone possessing a sulfonyl linkage (O=S=O); silicon resin having (—O—Si($CH_3$)$_2$—O—)$_n$; polyetherimide and polyethersulfone having an ether linkage (—C—O—C—)$_n$; phenoxy resin and cellulose resin having ether and hydroxyl (OH) groups; and polyacrylonitrile having nitrile (—CN) groups. Ester resin such as polyarylate; polyamide resin; polyamide-imide resin; polyurethane resin such as acrylic urethane; and polyetherimide resin which are hydrolyzed by being etched in a high concentration alkali solution to produce carboxyl groups, are also desirable.

However, resin such as polyethylene which does not have the above-described reaction zone, may also be used if it produces the functional groups due to carbon-carbon linkage cleaves or if carbon is oxidized under more severe etching conditions.

As described above, what type of etching treatment liquid is to be used depends upon the type of resin. When resins which originally have the above-described kinds of functional groups capable of being chemically bonded to metal, such as polyacrylonitrile having nitrile groups, are used, the metal can be chemically bonded to the resin even if an etching step is omitted.

Preferably, electroless treatment is performed to chemically bond the metal to the resin. Also, it is preferable to introduce a catalyst which promotes the reduction of the metal in order to chemically bond the metal to the resin. More preferably, a catalytic metal, such as Pd—Sn alloy, which serves as a catalyst for the electroless treatment, is introduced. In such a case, the catalytic metal is first bonded to the resin.

When a porous resin is etched as mentioned previously, the wettability between the metal and the porous resin improves with respect to the metallic solution. The solution containing the catalytic metal is permeated into the pores and the catalytic metal is chemically bonded to the resin, as indicated by the above reaction formulae (1) and (2). When the resin to which the catalytic metal is bonded is treated in a metallic solution containing metallic ions, complexing agents, and reducing agents, the metallic ions are reduced on the surface of the catalytic metal. Because other metals are bonded to the catalytic metal, and for other reasons, a metallic layer is uniformly formed around the nucleus of the catalytic metal.

Since the catalytic metal is chemically bonded to the porous resin, the amount of the catalytic metal increases, as does the amount of the metallic layer which can be subjected to the electroless treatment. The amount of the metallic layer can be controlled by changing the concentration of the etching treatment liquid, the etching treatment time, and the amount of metallic atoms or ions.

A metallic salt for generating the metallic ions during the electroless treatment is not limited as long as it is a water-soluble one, such as sulfate, chloride or nitrate. At least one of, for example, Ni, Co, Fe, Mo, W, Cu, Re, Au, Ag and Pt can be used as a conductive metal to be subjected to the electroless treatment and be used for coating a hollow fiber membrane. The precipitation amount of the above metal can be controlled by changing the concentration of the metallic ions, the temperature, and reaction time. The minimum level of the total amount of the metal to coat the resin membrane is determined from the viewpoint of achieving electrical conductivity necessary to enable energizing, and it is desirable that the maximum level of the total amount of the metal to coat the resin membrane is controlled from the viewpoint of not blocking the open pores of the resin membranes more than needed. As a reducing agent, known substances such as formalin and glucose are used as well as phosphorous compounds such as sodium hypophosphite, and boron compounds such as boron hydride. As a complexing agent, a type capable of forming complexes stable with metallic ions may be used, such as known substances like ammonia, citric acid, tartaric acid, and oxalic acid.

According to this invention, as the etching treatment liquid penetrates into the pores of the hollow fiber membrane, the metal is chemically bonded to the resin, thus penetrating into the surface as well as the inner walls of the resin pores. Accordingly, it is possible to make the thickness of the metallic layer 10–100% of the thickness of the resin membrane. It is also possible to increase the amount of the metal coating as much as $2.2 \times 10^{-3}$ to $15.0 \times 10^{-3}$ mol/m. A metallic layer which contains a large amount of metal improves the rigidity of the hollow fiber membrane and the pressure tightness required. Moreover, since the amount of metal coating is large, electrical conductivity can be enhanced.

Once the hollow fiber membrane acquires the electrical conductivity, it becomes possible to conduct an electrolytic treatment. It is possible to coat the metal to be electrolyzed (for example, Cr, Zn, Ag, Au, Pt, Al, Mn, Bi, Se, Te, Cd, Ir, Ti and Ni) over the above-mentioned metallic layer (electrolessly treated metallic layer).

When the metallic layer is chemically bonded to the resin, a sufficient amount of the metallic layer can be reliably formed. Therefore, it is possible to solder hollow fiber membranes to each other or to solder the hollow fiber membrane to the metal. Since the bond strength between the hollow fiber membrane and the metallic layer is strong, it is possible to prevent solder from peeling off the hollow fiber membrane at the interface between them, thus enabling complete and secure fixing of the hollow fiber membrane. This means that a large number of hollow fiber membranes can be modularized and a nucleic acid recovering device capable of processing a large amount can be provided.

As described previously, this invention is capable of further enhancing the electrical conductivity of the hollow fiber membrane because a sufficient amount of metal can be reliably formed on the hollow fiber membrane. In this invention, a hollow fiber membrane with a resistivity ranging from 1 to 20 $\Omega$/cm can be obtained, hence the electrical conductivity becomes extremely good. When the hollow fiber membrane is coated with a sufficient amount of the metallic layer with sufficiently high bond strength, the heat resistance of the hollow fiber membrane will be enhanced. Even if the hollow fiber membrane with low heat resistance (especially olefin type) is used, since the metallic layer can still be formed according to this invention, the heat resistant temperature of the hollow fiber membrane will be improved greatly. Accordingly, it is possible to utilize both sterilization by energizing and sterilization by heat treatment. For example, assuming that the heat resistant temperature of an untreated membrane on which no metallic layer is formed is approximately 70° C., it is possible to heighten the heat resistant temperature by 50° C. or more by forming the metallic layer.

In this invention, the inside diameter of the hollow fiber is, for example, 20–3000 $\mu$m, preferably 5–1000 $\mu$m. The film thickness of the hollow fiber membrane is, for example, 5–1000 $\mu$m, and the porosity is 3–15%, preferably being 5–7%.

DETAILED DESCRIPTION OF THE PREFERRED EMBODIMENTS

Figure 1:
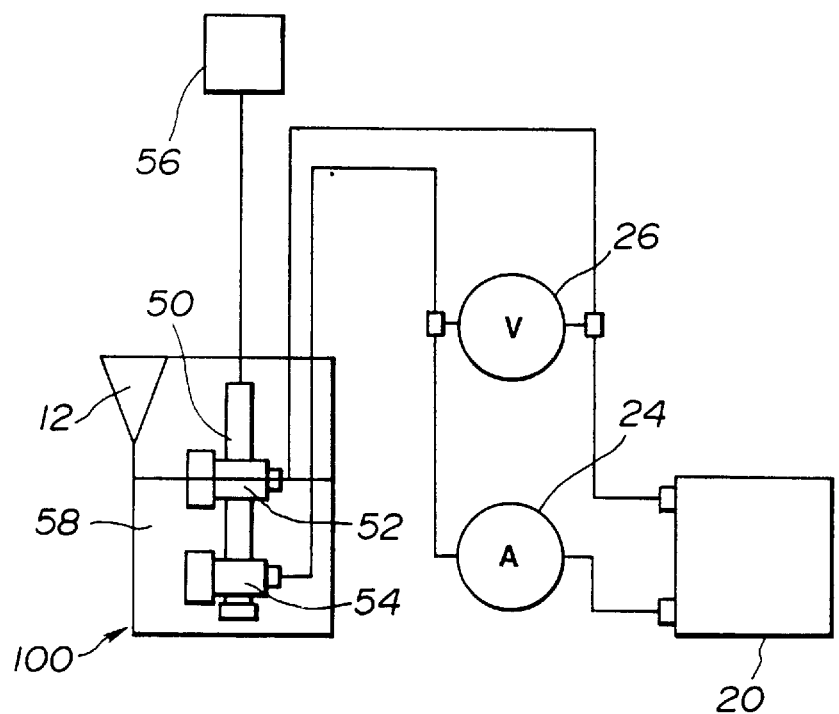
FIG. 1 is a block diagram of a nucleic acid recovering device of an embodiment of this invention.

FIG. 1 shows a model structure of the nucleic acid recovering device of this invention. This nucleic acid recovering device comprises: a body 100 comprising a container 12 which contains a solution 58, a hollow fiber membrane coated with metal 50, one end of which is blocked, and which is located in the container 12, and two terminals 52 and 54 mounted on the hollow fiber membrane coated with metal 50; a micropump 56 which is mounted at an upper end of the hollow fiber membrane coated with metal 50 and which draws up the solution 58 within the hollow fiber membrane coated with metal 50; and a pulse oscillator 20 which is connected to the terminals 52 and 54 and which sends pulse waves to the hollow fiber membrane coated with metal 50. Reference Numeral 24 indicates a pulse ammeter, and Reference Numeral 26 indicates a pulse voltmeter. These devices are capable of controlling the values of the applied electric current and voltage by monitoring the values of pulse current and pulse voltage during the sterilization treatment process.

The hollow fiber membrane coated with metal 50 has the construction of a hollow fiber membrane coated with a metal Ni. The formation of the metallic layer of Ni over the hollow fiber membrane is hereinafter explained.

A hollow fiber membrane made of porous polypropylene (manufactured by AKUZO) which is 1 mm in inside diameter and has 6% porosity was etched by being dipped in a mixed solution of 20–50% chromic acid ($CrO_3$) and 10–40% sulfuric acid (liquid temperature: 50°–75° C.) for several minutes. Then the hollow fiber membrane was dipped in a catalyst solution on the market (product called "Catalyst C" manufactured by Okuno Chemical Industries Co., Ltd.) for several minutes so as to have Pd chemically bonded to the hollow fiber membrane. After the Pd was activated by a weak acid solution of hydrochloric acid, a metallic layer of Ni was formed over the hollow fiber membrane by using an electroless nickel plating liquid sold on the market (a product called "TMP Chemical Nickel" manufactured by Okuno Chemical Industries Co., Ltd.). After the hollow fiber membrane with the metallic layer had been rinsed, it was dipped in an electroless plating liquid (a product called "OPC Electroless Gold" manufactured by Okuno Chemical Industries Co., Ltd.) so as to have Au coat the Ni layer. The specific resistance of the obtained hollow fiber membrane was measured as 0.5–1 Ωcm in average.

This embodiment is designed so as to send an electricity directly to the hollow fiber membrane coated with metal 50 through the two terminals 52 and 54.

Figure 2:
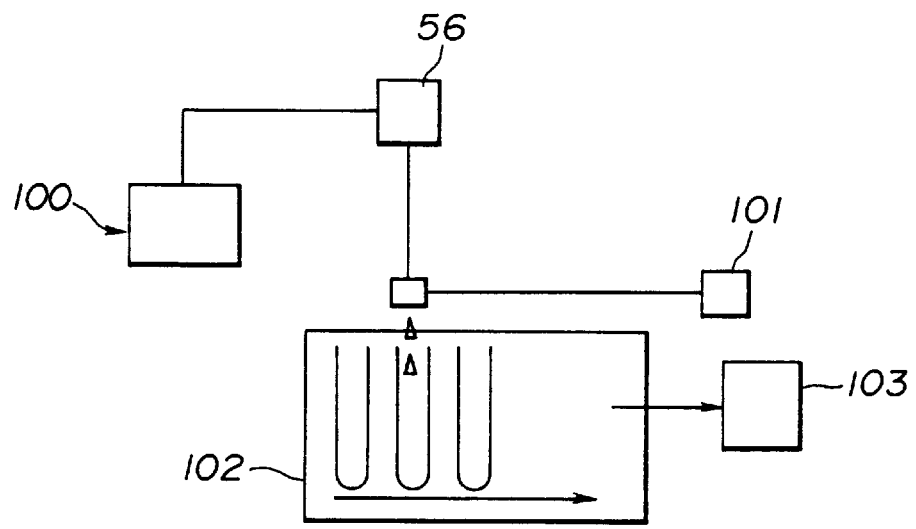
FIG. 2 is a schematic diagram showing the structure of the nucleic acid recovering device and peripheral equipment thereof according to the embodiment of this invention.

As shown in FIG. 2, a fraction collector 101 is connected to the micropump 56 so that the nucleic acid recovering device continuously recovers the recovered solution in predetermined test tubes which are located in the recovering device 102. Regarding the solution recovered in these test tubes, as later described in detail, the amount of nucleic acids and protein recovered is measured by using an absorptiometer 103.

Next, a nucleic acid recovering method by using the device of this invention is hereinafter explained.

The micro-organism, colibacillus (AHU 1719) (2–7 μm in diameter and 1–2 μm in breadth) which is a gram-negative Corynebacterium and which has been previously cultured, was prepared in the quantity of eight test tubes, twelve test tubes, and sixteen test tubes (each test tube should contain approximately $10^9$ pieces of colibacillus) and was diluted with physiological salt water so that the amount of salt water containing colibacillus in each of the above-mentioned three groups would become 50 ml. The above-mentioned eight test tubes of colibacillus diluted with physiological salt water form Sample A, the twelve test tubes of colibacillus diluted with physiological salt water form Sample B, and the sixteen test tubes of colibacillus diluted with physiological salt water form Sample C.

Three kinds of diluted solution 58 (Samples A, B and C) was respectively poured into the container 12, and the hollow fiber membrane coated with metal 50, on which the micropump 56 was mounted, was dipped in the solution 58. Then, the pulse oscillator 20 sent a pulse current of 200 mA to the hollow fiber membrane coated with metal 50 through the terminals 52 and 54. At the same time, the micropump 56 drew up the solution within the hollow fiber membrane coated with metal 50. The drawn-up solution was successively recovered into the test tubes in the amount of a hundred drops (about 3 ml) of the solution for each test tube, through the fraction collector 101. The solution recovered from Sample A was chronologically numbered as test tubes Nos. A-1 through A-5, the solution recovered from Sample B was chronologically numbered as Nos. B-1 through B-9, and the solution recovered from Sample C was chronologically numbered as test tubes Nos. C-1 through C-7.

Figure 3:
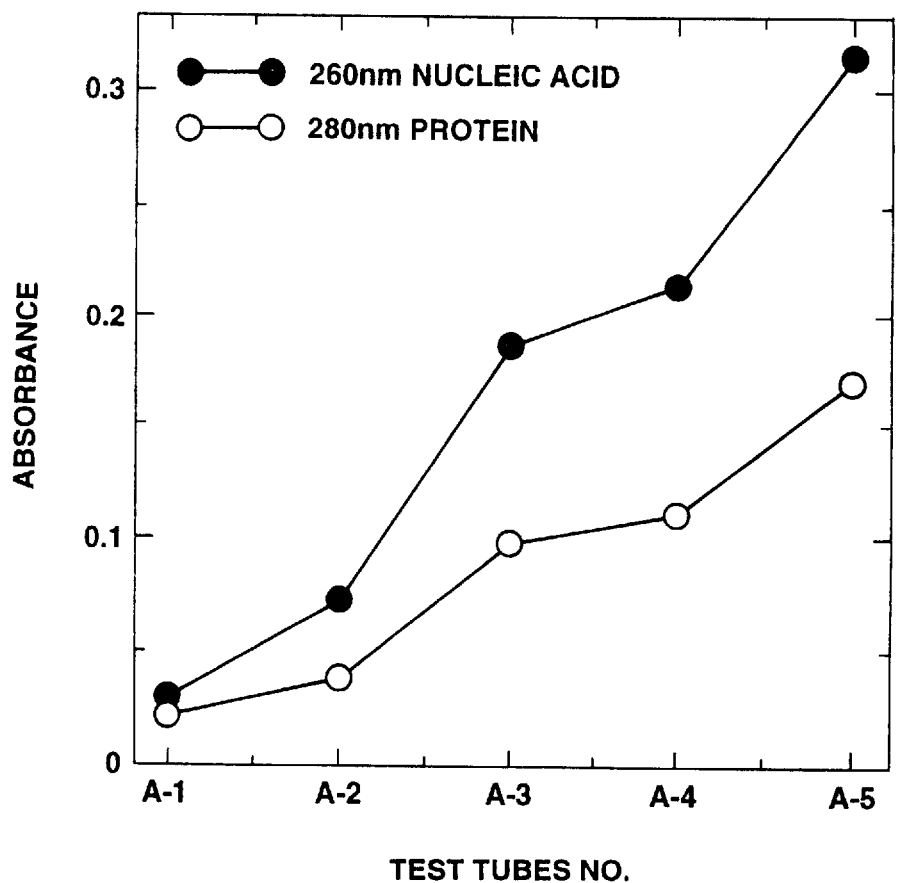
FIG. 3 is a chart showing the relationship between test tubes Nos. A-1 through A-5 and absorbance in the embodiment of the invention.
Figure 4:
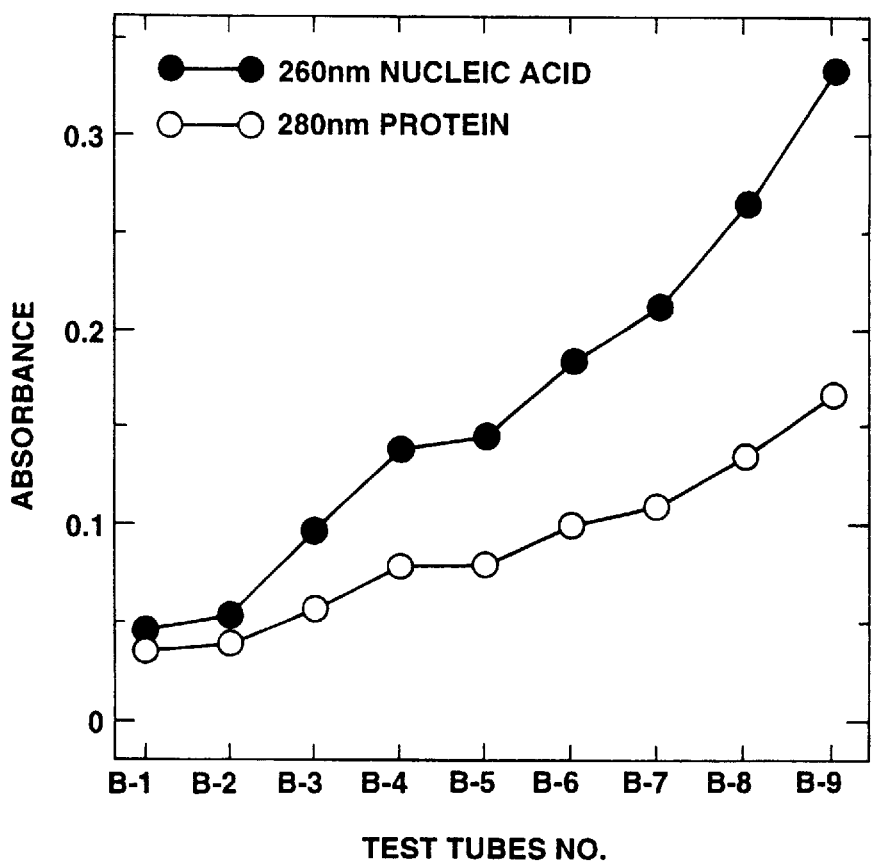
FIG. 4 is a chart showing the relationship between test tubes Nos. B-1 through B-9 and absorbance in the embodiment of the invention.
Figure 5:
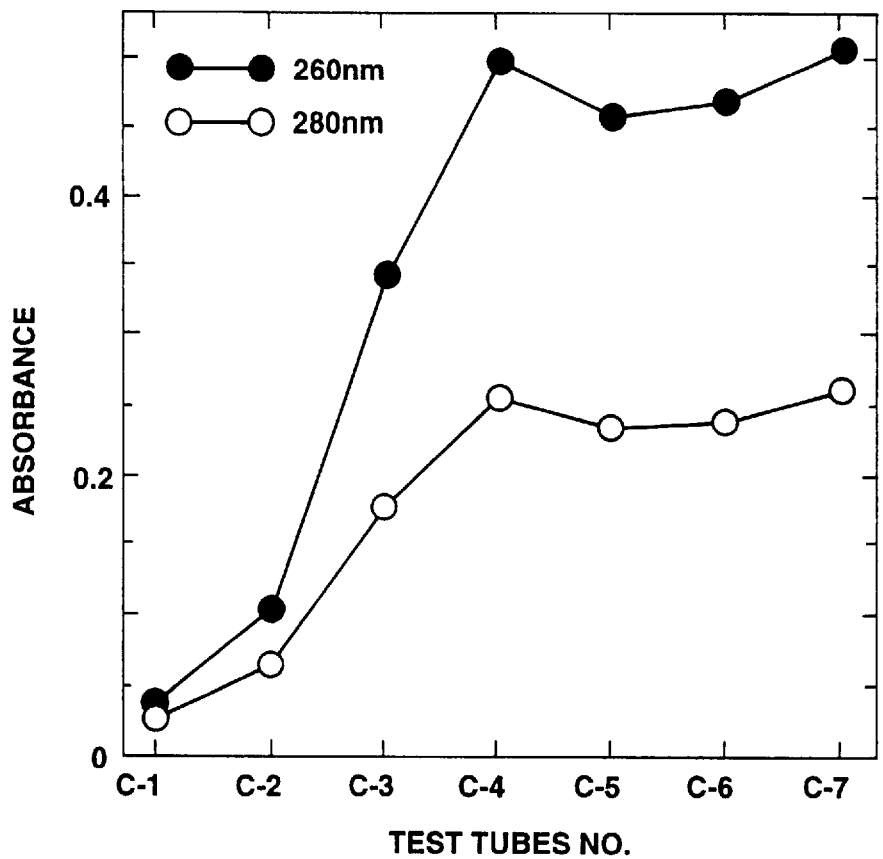
FIG. 5 is a chart showing the relationship between test tubes No. C-1 through C-7 and absorbance in the embodiment of the invention.

Next, an absorptiometer sold on the market was used to measure the amount of nucleic acids and protein contained in test tubes Nos. A-1 through A-5, B-1 through B-9, and C-1 through C-7. The measurement was conducted at the wavelength of 260 nm for nucleic acids and at the wavelength of 280 nm for protein. FIG. 3 shows the relationship between test tubes Nos. A-1 through A-5 and absorbance, FIG. 4 shows the relationship between test tubes Nos. B-1 through B-9 and absorbance, and FIG. 5 shows the relationship between test tubes Nos. C-1 through C-7 and absorbance.

FIGS. 3 through 5 show that as the total amount of the solution drawn up increases, the amount of recovered nucleic acids and protein also increases. This is because an accumulated layer of colibacillus is formed on the surface of the hollow fiber membrane coated with metal 50 as the total amount of the drawn-up solution increases. Therefore, it was confirmed that it is possible to recover both protein and nucleic acids. It was also confirmed that it is possible to recover nucleic acids better than protein.

The protein and nucleic acids contained in the recovered solution can be separated by using, for example, a liquid chromatography or thin layer chromatography, etc.

As a result of examinations to see whether colibacillus is contained in the above-mentioned recovered solution, it was found that the solution contained no colibacillus. Accordingly, one can tell that it is possible to continuously decompose colibacillus and recover nucleic acids by sending pulse waves to the solution containing colibacillus and then making the solution pass through the hollow fiber membrane.

If the solution drawn up by the micropump 56 is connected to a device for fractioning nucleic acids such as a high performance liquid chromatograph, it is possible to fraction nucleic acids continuously.

Subsequently, Sample A was recovered in test tubes in the same manner as described above, which were numbered chronologically as test tubes Nos. 1–6. The amount of nucleic acids and protein contained in test tubes Nos. 1–6 was measured in the same manner as described above, except that a direct current of 500 mA was sent to the hollow fiber membrane coated with metal 50. The results of this measurement are shown in FIG. 6.

Figure 6:
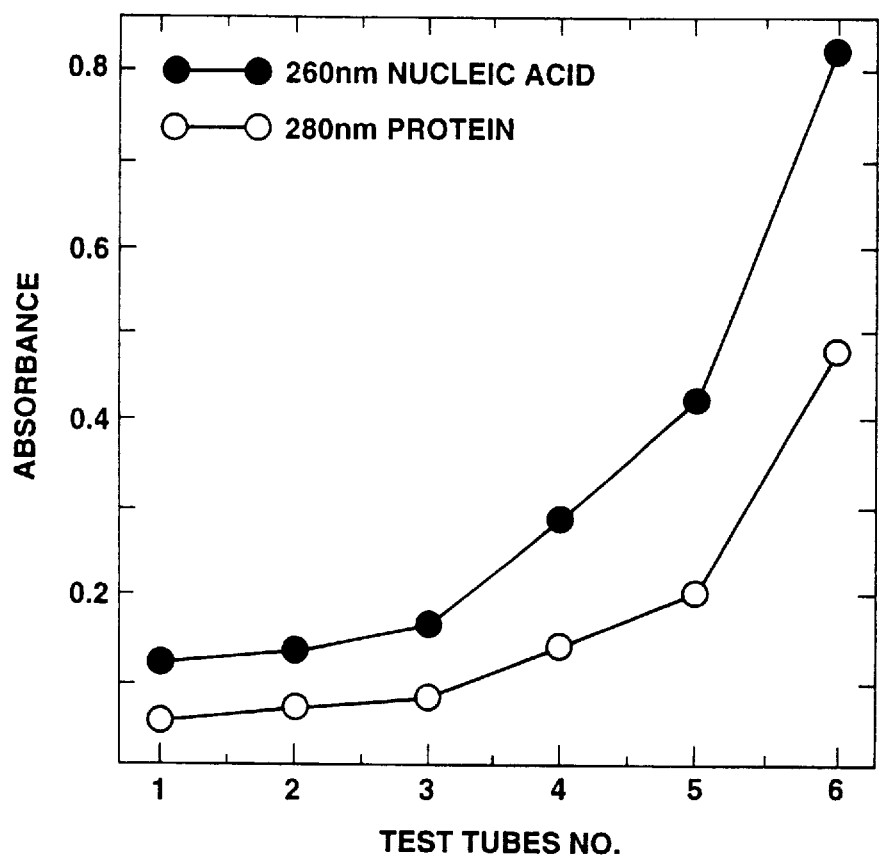
FIG. 6 is a chart showing the relationship between test tubes Nos. 1–6 in the embodiment of the invention.

FIG. 6 shows that although the first one to three test tubes cannot obtain a large recovery percentage, an accumulated layer of colibacillus is formed over the hollow fiber membrane coated with metal 50 as the total amount of the drawn-up solution increases, and therefore the recovery efficiency per test tube is especially high in the test tube No. 6. Similar to the results shown in FIGS. 3 through 5, it was also confirmed that nucleic acids can be recovered better than protein.

As described above, although nucleic acids have been recovered in plural operations by conventional methods, the embodiment of this invention allows nucleic acids to be efficiently recovered immediately after sterilization of colibacillus, thus enabling continuous recovery of nucleic acids. Although pulse waves or direct current was sent through the solution containing colibacillus in the above-described embodiment, the type of electricity that can be sent is not limited to those used above. For example, impulse waves or alternating current may be used. Moreover, the type of micro-organisms that can be contained in the solution is not limited to colibacillus as used in the above-mentioned embodiment and, for example, other micro-organisms which act as hosts of gene recombination such as Bacillus subtilis, human culture cells, Hela cells (cells from human uterocervical cancer), FL cells (cells from human fetal amniotic cellular structure), and Vero cells (cells from African green monkey's renal cells) may be used.

The structure of the electrodes is not limited to the hollow fiber membrane coated with conductive metal as used in the embodiment of this invention, and electrodes having other structures may be used as long as they can energize the solution containing micro-organisms.

The type of the energizing device to send an electricity to the electrodes is not limited to the pulse oscillator as used in the embodiment of this invention, and other types of devices capable of sending electricity to the electrodes may be used, such as a direct current electricity source or impulse generator.

Another embodiment of this invention is hereinafter explained. In this embodiment, nucleic acids were recovered by the method described below and by using direct current instead of the pulse oscillator 20 of the nucleic acid recovering device as shown in FIG. 1, a direct current ammeter instead of the pulse ammeter, and a direct current voltmeter instead of the pulse voltmeter.

FL cells were used as micro-organisms and were cultured in a culture bottle (5 ml). After the cultured cells were exfoliated by a trypsin EDTA solution and were dispersed, the cells were rinsed with Hank's BSS, thereby obtaining a cell floating liquid of a fixed concentration. This cell floating liquid was poured into an Eppendorf centrifuging tube (volume: 1.5 ml), a conductive hollow fiber membrane which had been subjected to alcohol substitution was dipped in the cell floating liquid, and the liquid within the hollow fiber membrane was drawn up while sending a direct current of 100 mA to the hollow fiber membrane.

Figure 7:
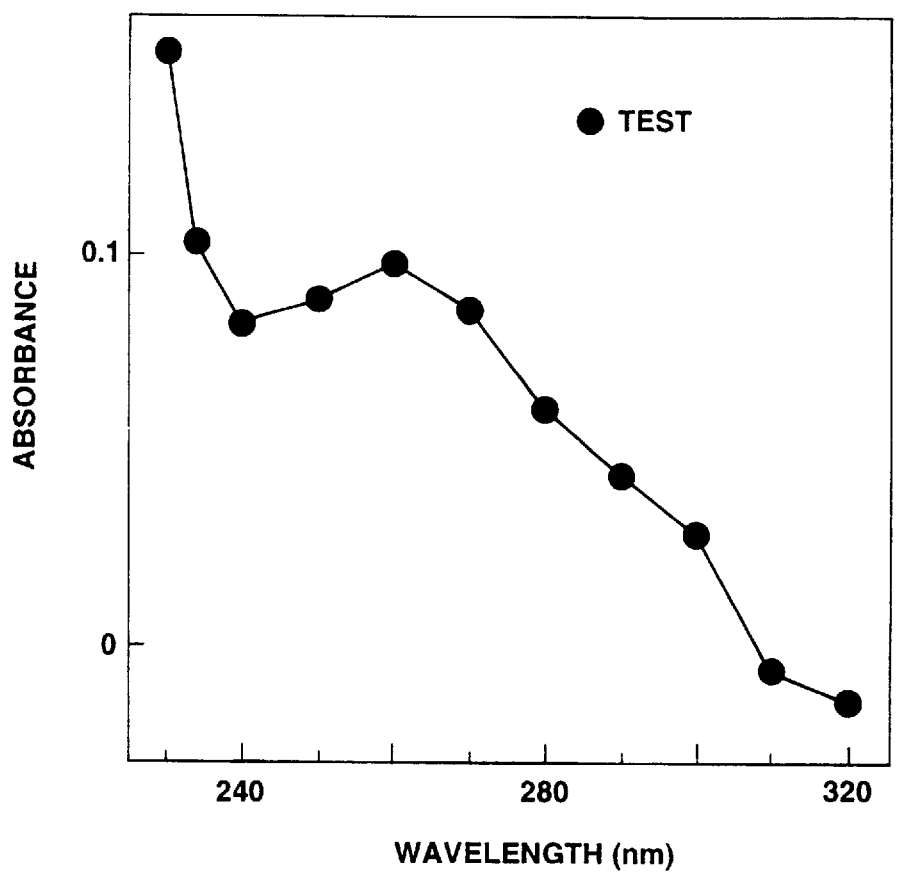
FIG. 7 displays a chart showing the relationship between the wavelength and absorbance of the recovered liquid in another embodiment of the invention.

The purity of the nucleic acids drawn up and recovered was examined according to the values measured by applying absorption wavelength of 280 nm, 260 nm and 235 nm. The measurement of absorbance was conducted by using quartz cells and a spectrophotometer manufactured by HITACHI, LTD. The results of the measurement are shown in FIG. 7.

In order to compare the efficiency of nucleic acid recovery, InstaGenematrix manufactured by BIO-RAD was used to purify and recover nucleic acids, and the purity of the recovered nucleic acids was examined in the same manner as described above. The results of this measurement are shown in FIG. 8.

The process of recovering nucleic acids by InstaGenematrix is as follows:

FL cells were used as a sample. After FL cells were rinsed and condensed with phosphoric acid buffer salt water (PBS), the FL cells were caused to float in distilled water again. InstaGene was added to the sample, which was then incubated for 30 minutes at a temperature of 56° C. At this stage, InstaGene broke the enzymes of the cells and caused agglutination of nucleic acids (gene). Next, a heat treatment was conducted for 8 minutes at a temperature of 100° C. to cause thermal denaturation of enzymes and other protein and agglutination of nucleic acids. The obtained solution was mixed well so as to be used as a sample for gene amplification (PCR).

Figure 8:
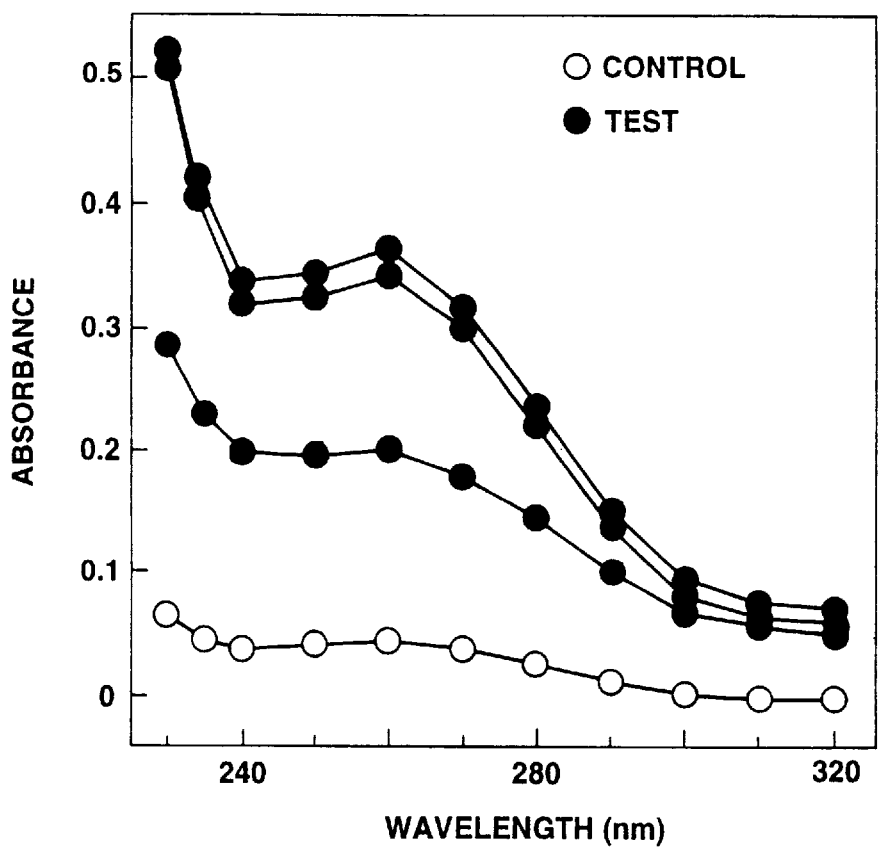
FIG. 8 displays a chart showing the relationship between the wavelength and absorbance of the recovered liquid for comparison in another embodiment of the invention.

FIGS. 7 and 8 show that almost the same recovery pattern is obtained both in the case of the recovery of nucleic acids by using the hollow fiber membrane coated with metal (conductive hollow fiber membrane) contained in the embodiment of this invention and in the case of the recovery of nucleic acids by using a chemical product available in the market. However, the absorbance indicated on the vertical axis of FIG. 7 differs from that of FIG. 8 because the concentration of the cells used in each sample was different. When a sample of the same cell concentration was used, almost the same amount of nucleic acids was recovered. When the above-described drawing and recovery were conducted without energizing the hollow fiber membrane coated with metal of the aforementioned embodiment, a pattern similar to the pattern indicated as CONTROL in FIG. 8 was obtained.

The results shown in these figures were obtained by performing the measurement while changing the absorption wavelength for each 10 nm from 230 nm to 320 nm in order to examine the purity of the recovered sample. According to such results, one can tell that both in the case of the hollow fiber membrane coated with metal of the embodiment of the invention and in the case of InstaGenematrix, the absorbance apparently shows its peak value when the absorption wavelength is 260 nm which is the value set for nucleic acids, and also shows a high peak when the absorption wavelength is 230 nm which is the absorption wavelength zone of polysaccharide. Concerning the purity of the sample, the above results show that impurities are mixed in the solution. However, that does not cause any problem as long as the sample is used for amplification of nucleic acids.

Then, whether or not protein is mixed in the solution was examined. The proportion of the absorbance at the wavelength of 260 nm to that of 280 nm was approximately 2.000 when the hollow fiber membrane coated with metal was used and the solution was drawn up by sending a direct current of 100 mA. On the other hand, when InstaGenematrix was used, the proportion of 260 nm to 280 nm was approximately 1.600.

Generally when the cells are broken and then nucleic acids are recovered from the broken cells, if a large amount of protein is mixed in the recovered nucleic acids, it means that many protein enzymes are present. In this case, there is a possibility that the recovered nucleic acids may be decomposed by these protein enzymes. Accordingly, a proportion of the amount of protein to the amount of nucleic acids contained in the recovered sample is the subject of the recovery of nucleic acids. The value of this proportion can be obtained, as described above, by measuring the absorbance of the obtained sample at the absorption wavelength of 260 nm and 280 nm, and then calculating the proportion of the results of 260 nm to 280 nm. If the proportion is 1.400 or higher, one may say that mixing of protein is controlled to some extent.

In the embodiment of the invention, the proportion of 260 nm to 280 nm showed a value which is much higher than the standard value (1.400) and which is better than the case of InstaGenematrix. As a result, it was proved that the hollow fiber membrane coated with metal of the embodiment of this invention is appropriate as the device for collecting nucleic acids from cells.

Figure 9:
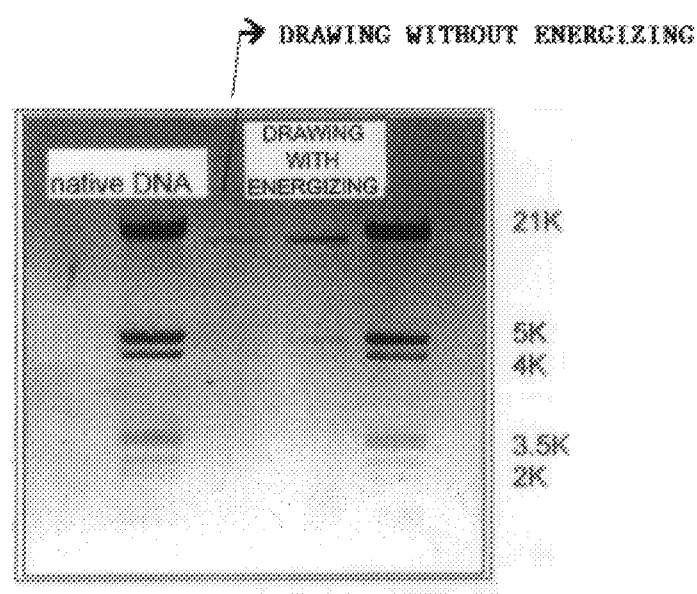
FIG. 9 is a drawing showing migration patterns of the recovered liquid in another embodiment of the invention.

The recovered solution which was obtained in the embodiment of this invention was further analyzed by agarose gel electrophoresis and pulse field gel electrophoresis. Moreover, in order to examine whether or not the nucleic acids to be recovered suffer physical damages when passing through the hollow fiber membrane coated with metal, for the purpose of comparison, standard genes of Lambda phage DNA were drawn up and recovered in the same manner as in the embodiment of the invention, and were analyzed by agarose gel electrophoresis and pulse field gel electrophoresis. FIG. 9 shows migration patterns obtained as a result of the above analysis. FIG. 9 indicates that the nucleic acids drawn up through the hollow fiber membrane coated with metal of the embodiment of the invention shows a migration pattern similar to that of the comparison band (native DNA), although the recovered amount of the nucleic acids is smaller than in the case of native DNA. As a result, it was proved that the nucleic acids recovered do not suffer any physical damage when the cells are drawn up by using the hollow fiber membrane of the embodiment of the invention while performing the energizing treatment. The same results were obtained for Hela cells and Vero cells. The numerical values such as 21K, 5K and 4K on the right side of FIG. 9 show the number of base-pairing configurations in the sample. For example, 21K means 21000 base-pairing sequences (B.P.S.).

When the above-mentioned sample was drawn up and recovered without sending electricity to the hollow fiber membrane, the amount of nucleic acids in the recovered sample was less than that of the case when energizing was conducted. This is because absorption of nucleic acids into the hollow fiber membrane coated with metal caused by energizing does not occur if energizing is not conducted. The above fact also proves that the hollow fiber membrane coated with metal of the embodiment of the invention is a superior device for recovering nucleic acids.

As described above, this invention makes it possible to recover nucleic acids continuously in one operation by sending electricity through a solution containing micro-organisms. It is also possible to easily recover only the nucleic acids by filtering the micro-organisms off the energized solution and drawing up the filtered solution.

This invention also makes it possible to recover both nucleic acids and protein continuously in one operation by sending electricity through the solution containing the micro-organisms.

Furthermore, it is possible to recover nucleic acids more efficiently by sending pulse waves or direct current through the solution containing the micro-organisms.

What is claimed is:

1. The method of recovering nucleic acids from microorganisms in a solution, comprising:
    applying the solution to a microporous resin member which is coated by conductive metal;
    applying an electric current to said metal coated on said resin member in an amount effective to extract said nucleic acids from said microorganisms;
    and recovering the nucleic acids extracted.

2. The method for recovering nucleic acids according to claim 1, wherein the pulse waves are sent as said electric current.

3. The method for recovering nucleic acids according to claim 1, wherein direct current is sent as said electric current.

4. The method of recovering nucleic acids from microorganisms in a solution comprising:
    applying the solution to a hollow fiber that is coated by a conductive metal;
    supplying an electric current to the metal coated on the fiber in an amount effective to extract said nucleic acids from said microorganisms;
    and recovering the nucleic acids extracted.

5. The method of claim 4, wherein the conductive metal is chemically bonded to the hollow fiber.

6. The method of recovering protein from microorganisms in a solution comprising:
    applying the solution to a microporous resin member which is coated by conductive metal;
    applying an electric current to said metal coated on said resin member in an amount effective to extract said protein from said microorganisms;
    and recovering the protein extracted.

7. The method for recovering protein according to claim 6, wherein the pulse waves are sent as said electric current.

8. The method for recovering protein according to claim 6, wherein direct current is sent as said electric current.

9. The method of recovering protein from microorganisms in a solution, comprising:
    applying the solution to a hollow fiber that is coated by a conductive metal;
    supplying an electric current to the metal coated on the fiber in an amount effective to extract said protein from said microorganisms;
    and recovering the protein extracted.

10. The method of claim 9, wherein the conductive metal is chemically bonded to the hollow fiber.

* * * * *